(12) United States Patent
Ohkubo

(10) Patent No.: US 11,827,578 B2
(45) Date of Patent: Nov. 28, 2023

(54) METHOD FOR PRODUCING OXIDATION REACTION PRODUCT OF HYDROCARBON OR DERIVATIVE THEREOF

(71) Applicant: OSAKA UNIVERSITY, Suita (JP)

(72) Inventor: Kei Ohkubo, Osaka (JP)

(73) Assignee: Osaka University, Osaka (JP)

( * ) Notice: Subject to any disclaimer, the term of this patent is extended or adjusted under 35 U.S.C. 154(b) by 410 days.

(21) Appl. No.: 17/253,438

(22) PCT Filed: Jun. 18, 2019

(86) PCT No.: PCT/JP2019/024155
§ 371 (c)(1),
(2) Date: Jul. 16, 2021

(87) PCT Pub. No.: WO2019/244899
PCT Pub. Date: Dec. 26, 2019

(65) Prior Publication Data
US 2021/0403395 A1    Dec. 30, 2021

(30) Foreign Application Priority Data
Jun. 20, 2018 (JP) .................................. 2018-117453

(51) Int. Cl.
*C07C 33/00* (2006.01)
*C07C 51/29* (2006.01)
(Continued)

(52) U.S. Cl.
CPC .............. *C07B 33/00* (2013.01); *C07C 29/48* (2013.01); *C07C 45/30* (2013.01); *C07C 51/16* (2013.01); *C07C 51/29* (2013.01)

(58) Field of Classification Search
CPC ......... C07B 33/00; C07C 29/48; C07C 45/30; C07C 51/29; C07C 51/16
See application file for complete search history.

(56) References Cited

U.S. PATENT DOCUMENTS

2019/0315936 A1    10/2019  Takamori et al.
2020/0377453 A1*   12/2020  Takamori ................ C07C 37/60

FOREIGN PATENT DOCUMENTS

EP     3 398 925        11/2018
JP     6080281 B        2/2017
(Continued)

OTHER PUBLICATIONS

Methane, Safety Data Sheet (SDS), [Online], Takachiho Chemical Industrial Co., Ltd., Oct. 1, 2015, Internet:<URL: https://www.takachiho.biz/pdf/CH4.pdf>—see the Machine translation of the Decision of Refusal for a concise explanation.
(Continued)

*Primary Examiner* — Yate' K Cutliff
(74) *Attorney, Agent, or Firm* — Hamre, Schumann, Mueller & Larson, P.C.

(57) ABSTRACT

The present invention is intended to provide a method that can produce an oxidation reaction product of a hydrocarbon or a derivative thereof in an aqueous phase using a hydrocarbon or a derivative thereof as a raw material. In order to achieve the above object, the method for producing an oxidation reaction product of a hydrocarbon or a derivative thereof of the present invention includes the step of: irradiating a reaction system with light in a presence of a raw material and a halogen oxide radical to react, wherein the raw material is a hydrocarbon or a derivative thereof, the reaction system is a reaction system containing an aqueous phase, the aqueous phase contains the raw material and the halogen oxide radical, and in the reaction step, the raw material is oxidized to produce an oxidation reaction product of the raw material.

11 Claims, 1 Drawing Sheet

(51) Int. Cl.
  *C07B 33/00* (2006.01)
  *C07C 29/48* (2006.01)
  *C07C 45/30* (2006.01)
  *C07C 51/16* (2006.01)

(56) References Cited

FOREIGN PATENT DOCUMENTS

| WO | 2017/104798 | 6/2017 |
|---|---|---|
| WO | 2018/088494 | 5/2018 |
| WO | 2018/110710 | 6/2018 |
| WO | 2019/151535 | 8/2019 |

OTHER PUBLICATIONS

Ethane, Safety Data Sheet (SDS), [Online], Takachiho Chemical Industrial Co., Ltd., Apr. 28, 2016, Internet:<URL: https://www.takachiho.biz/pdf/C2H6.pdf>—see the Machine translation of the Decision of Refusal for a concise explanation.

Propane, Safety Data Sheet (SDS), [Online], Takachiho Chemical Industrial Co., Ltd., Nov. 2, 2015, Internet: <URL:https://www.takachiho.biz/pdf/C3H8.pdf>—see the Machine translation of the Decision of Refusal for a concise explanation.

Decision of Refusal for the corresponding Japanese Patent Application No. 2020-525753 dated May 10, 2022, 8 pages with machine translation.

Long et al., "Oxidation of ethane to ethanol by N2O in a metal-organic framework with coordinatively unsaturated iron (II) sites", Nature Chemistry, vol. 6, pp. 590-595, 2014.

Süss-Fink et al., "Hydrogen Peroxide Oxygenation of Alkanes Including Methane and Ethane Catalyzed by Iron Complexes in Acetonitrile", Advanced Synthesis & Catalysis, vol. 346, pp. 317-332, 2004.

Snyder et al., "The active site of low-temperature methane hydroxylation in iron-containing zeolites", Nature, vol. 536, pp. 317-321, 2016.

International Search Report issued in International Application No. PCT/JP2019/024155, dated Sep. 17, 2019, 4 pages with translation.

Office Action issued in corresponding European Patent Application No. 19822913.0, dated Jul. 5, 2023, 4 pages \* cited by examiner

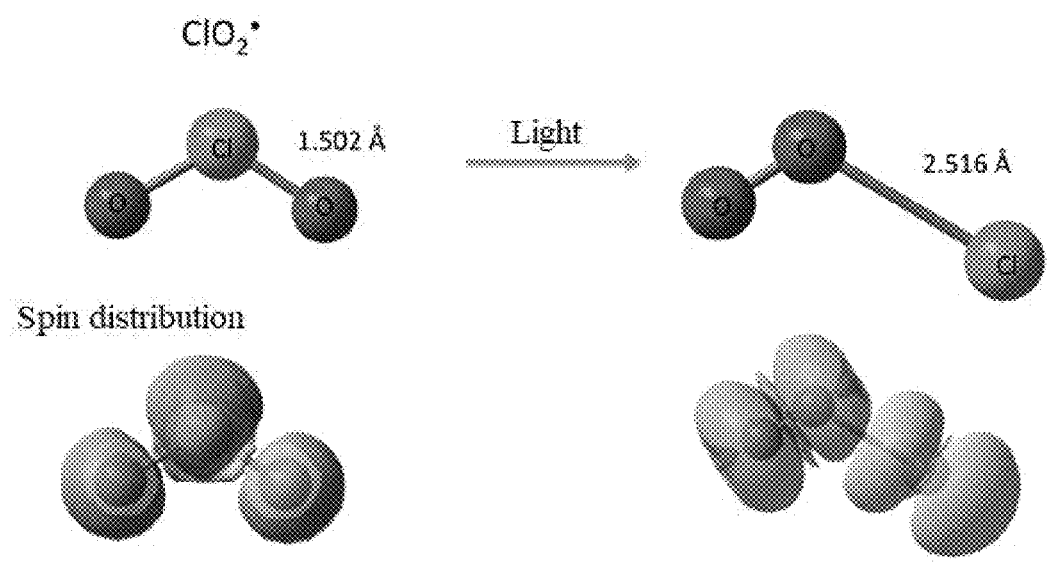

METHOD FOR PRODUCING OXIDATION REACTION PRODUCT OF HYDROCARBON OR DERIVATIVE THEREOF

TECHNICAL FIELD

The present invention relates to a method for producing an oxidation reaction product of a hydrocarbon or a derivative thereof.

BACKGROUND ART

Alcohol, carboxylic acid, and the like, which are of great use in terms of industrial application, are produced industrially by various kinds of methods. For example, as a method for producing methanol, a method of reacting carbon monoxide obtained by partial combustion of hydrocarbon with hydrogen gas at a high temperature and a high pressure is commonly used. Carbon monoxide and hydrogen gas, which are raw materials, can be produced, for example, by partial combustion of methane (natural gas), steam reforming, and the like. Also, alcohol, carboxylic acid, and the like are commonly produced by a biochemical method such as fermentation.

Furthermore, in these years, for the effective use of natural gas such as shale gas, a method is proposed for producing an oxidation reaction product such as alcohol by oxidizing hydrocarbon contained in natural gas. As a method for producing an oxidation reaction product by a gas phase reaction, for example, there is a method for producing ethanol by oxidizing ethane with dinitrogen monoxide in the presence of an iron catalyst (Non Patent Literature 1). As a method for producing an oxidation reaction product by a liquid phase reaction, there is a method for producing methanol by oxidizing methane by hydrogen peroxide in an acetonitrile solvent in the presence of an iron catalyst (Non Patent Literature 2).

CITATION LIST

Non Patent Literature

Non Patent Literature 1: Jeffrey R. Long and co-workers Nature Chem. 2014, 6, 590
Non Patent Literature 2: Georg Suss-Fink and co-workers Adv. Synth. Catal. 2004, 346, 317

SUMMARY OF INVENTION

Technical Problem

The production process of carbon monoxide by partial combustion of hydrocarbon, however, has a problem of spewing large amounts of carbon dioxide (greenhouse gas). Also, the production of an oxidation reaction product by a biochemical method such as fermentation has a problem of requiring great amounts of energy in fertilization, crop-dusting, harvesting, and transport in the process of cultivating raw material crops (e.g., maize), for example. Furthermore, these methods cannot produce alcohol, carboxylic acid, and the like using hydrocarbon as a raw material, and thus are not suitable for effective use of hydrocarbon contained in natural gas.

On the other hand, a method for producing an oxidation reaction product using hydrocarbon as a raw material can perform a reaction in an organic solvent. If this reaction can be performed in the aqueous phase, cost reduction can be expected.

With the foregoing in mind, it is an object of the present invention to provide a method that can produce an oxidation reaction product of a hydrocarbon or a derivative thereof in an aqueous phase using a hydrocarbon or a derivative thereof as a raw material.

Solution to Problem

In order to achieve the above object, the present invention provides a method for producing an oxidation reaction product of a hydrocarbon or a derivative thereof including the step of: irradiating a reaction system with light in the presence of a raw material and a halogen oxide radical to react, wherein the raw material is a hydrocarbon or a derivative thereof, the reaction system is a reaction system containing an aqueous phase, the aqueous phase contains the raw material and the halogen oxide radical, and in the reaction step, the raw material is oxidized by the light irradiation to produce an oxidation reaction product of the raw material.

In the following, the method for producing an oxidation reaction product of a hydrocarbon or a derivative thereof of the present invention may simply be referred to as a "production method of the present invention".

Advantageous Effects of Invention

According to the production method of the present invention, using a hydrocarbon or a derivative thereof as a raw material, an oxidation reaction product of the hydrocarbon or the derivative thereof can be produced in an aqueous phase.

BRIEF DESCRIPTION OF DRAWINGS

FIG. 1 is an example of prediction based on the result of the density functional calculation by UCAM-B3LYP/6-311+G(d, p) def2TZV when a chlorine dioxide radical ($ClO_2\cdot$) is irradiated with light.

DESCRIPTION OF EMBODIMENTS

The present invention will be described below in more detail with reference to illustrative examples. The present invention, however, is by no means limited thereby.

In the reaction step of the production method of the present invention, for example, at least the aqueous phase may be irradiated with light.

In the production method of the present invention, for example, the halogen oxide radical may be a chlorine dioxide radical.

The production method of the present invention may further include the step of generating the halogen oxide radical, for example.

In the production method of the present invention, for example, a reaction system of the halogen oxide radical generation step may contain an aqueous phase, and in the halogen oxide radical generation step, the aqueous phase may contain a source of the halogen oxide radical and the halogen oxide radical may be generated from the source of the halogen oxide radical.

In the halogen oxide radical generation step of the production method of the present invention, for example, at least one of a Lewis acid or a Brønsted acid may be caused to act on the source of the halogen oxide radical to generate the halogen oxide radical.

In the production method of the present invention, for example, the halogen oxide radical may be a chlorine dioxide radical, and, in the halogen oxide radical generation step, the source of the chlorine dioxide radical may be chlorite ion ($ClO_2^-$).

In the reaction step of the production method of the present invention, for example, the reaction may be performed in a state where oxygen ($O_2$) is present in the reaction system.

The production method of the present invention may be performed, for example, in an atmosphere having a temperature between $-100°$ C. and $200°$ C. and a pressure between 0.1 and 10 MPa. Furthermore, the production method of the present invention may be performed, for example, in an atmosphere having a temperatures between $0°$ C. and $40°$ C. and a pressure between 0.1 and 1.0 MPa or between 0.1 and 0.5 MPa.

In the production method of the present invention, for example, the raw material may be at least one selected from the group consisting of methane, ethane, and propane.

In the production method of the present invention, for example, the oxidation reaction product of the raw material may be at least one selected from the group consisting of alcohols, carboxylic acids, aldehydes, ketones, percarboxylic acids, and hydroperoxides.

In the production method of the present invention, for example, the hydrocarbon in the raw material may be a saturated hydrocarbon. The saturated hydrocarbon may be, for example, methane, ethane, or propane, as described above, or may be, for example, cyclohexane or the like.

In the production method of the present invention, for example, the hydrocarbon in the raw material may be a non-aromatic unsaturated hydrocarbon.

In the production method of the present invention, for example, the hydrocarbon in the raw material may be an aromatic hydrocarbon. The aromatic hydrocarbon may be, for example, benzene.

In the production method of the present invention, when the hydrocarbon in the raw material is a saturated hydrocarbon or a non-aromatic unsaturated hydrocarbon, for example, the oxidation reaction product may be at least one selected from the group consisting of alcohols, carboxylic acids, aldehydes, ketones, percarboxylic acids, and hydroperoxides as described above.

In the production method of the present invention, when the hydrocarbon in the raw material is methane, for example, the oxidation reaction product may contain at least one of methanol, formic acid, formaldehyde, and methyl hydroperoxide.

In the production method of the present invention, when the hydrocarbon in the raw material is ethane, for example, the oxidation reaction product may contain at least one of ethanol, acetic acid, acetaldehyde, and ethyl hydroperoxide.

In the production method of the present invention, when the hydrocarbon in the raw material is propane, for example, the oxidation reaction product may contain at least one of 1-propanol, 2-propanol (isopropyl alcohol), propionic acid, propionaldehyde, acetone, and propyl hydroperoxide.

In the production method of the present invention, when the hydrocarbon in the raw material is cyclohexane, for example, the oxidation reaction product may contain at least one of cyclohexanol, cyclohexanone, cyclohexane hydroperoxide, and a ring-opening oxide (e.g., adipic acid).

In the production method of the present invention, when the hydrocarbon in the raw material is an aromatic hydrocarbon, for example, the oxidation reaction product may contain at least one of phenol and quinone. It is to be noted that, while "phenol" denotes both hydroxy benzene and aromatic hydroxy compounds in general (including hydroxy benzene) each obtained by substituting a hydrogen atom of an aromatic (e.g., aromatic hydrocarbon or heteroaromatic) nucleus with a hydroxy group, the "phenol" denotes the latter in the present invention, unless otherwise stated. Furthermore, while "quinone" denotes both p-benzoquinone and dicarbonyl compounds in general (including p-benzoquinone and o-benzoquinone) obtained by substituting two hydrogen atoms of an aromatic ring (e.g., a benzene ring) in an aromatic (e.g., aromatic hydrocarbon or heteroaromatic) with two oxygen atoms, the "quinone" denotes the latter in the present invention, unless otherwise stated.

In the production method of the present invention, when the hydrocarbon in the raw material is benzene, for example, the oxidation reaction product may contain at least one of hydroxybenzene, p-benzoquinone, o-benzoquinone, hydroquinone, resorcinol, and catechol.

More specifically, the production method of the present invention can be performed, for example, as follows.

[1. Hydrocarbon or Derivative Thereof]

First, a hydrocarbon or a derivative thereof, which is a raw material (substrate), is provided. The raw material may be a hydrocarbon itself, or a derivative thereof.

The hydrocarbon is not particularly limited, and may be, for example, a non-aromatic or aromatic, or may be saturated or unsaturated. More specifically, the hydrocarbon may be, for example, a straight-chain or branched saturated or unsaturated hydrocarbon (e.g., a straight-chain or branched alkane, a straight-chain or branched alkene, or a straight-chain or branched alkyne). Further, the hydrocarbon may be, for example, a saturated or unsaturated hydrocarbon containing a non-aromatic ring structure (e.g., a cycloalkane, a cycloalkene). Further, the hydrocarbon may be an aromatic hydrocarbon. In addition, the hydrocarbon may or may not have one or more aromatic or non-aromatic rings in its structure, and may or may not have one or more hydrocarbon groups of a straight-chain or branched saturated or unsaturated hydrocarbon in its structure. Specific examples of the hydrocarbon include methane, ethane, propane, n-butane, 2-methylpropane, n-pentane, n-hexane, ethylene, propylene, 1,3-butadiene, acetylene, cyclopentane, cyclohexane, cycloheptane, cyclooctane, methyl cyclohexane, cyclohexene, benzene, toluene, o-xylene, m-xylene, p-xylene, mesitylene, durene, biphenyl, naphthalene, 1-methyl naphthalene, 2-methyl naphthalene, anthracene, phenanthrene, pyrene, and styrene.

In the present invention, a "derivative" of the hydrocarbon is an organic compound containing a hetero element (an element other than carbon and hydrogen). The hetero element is not particularly limited, and examples thereof include oxygen (O), nitrogen (N), sulfur (S), and halogen. Examples of the halogen include fluorine (F), chlorine (Cl), bromine (Br), and iodine (I). The derivative may be, for example, an organic compound having a structure in which a hydrocarbon group is bonded to a freely selected substituent or a freely selected atomic group. Further, the derivative may be, for example, a compound having a structure in which a plurality of hydrocarbon groups are bonded by a freely selected atomic group, and the hydrocarbon group may or may not be substituted with one or more substituents. Then, the portion of the hydrocarbon group may be oxidized by an oxidation reaction in the reaction step to produce an oxidation reaction product of a derivative of the hydrocarbon. The hydrocarbon group is not particularly limited, and may be, for example, a monovalent or bivalent or more group derived from the hydrocarbon. In the hydrocarbon group, one or more carbon atoms may be substituted with hetero atoms, for example. Specifically, for example, one carbon atom (and hydrogen atoms bonded thereto) of a phenyl group may be substituted with a nitrogen atom to form a pyridyl group. The substituent or atomic group is not particularly limited, and examples thereof include a hydroxy group, halogen group (a fluoro group, a chloro group, a bromo group, an iodo group, or the like), an alkoxy group, an aryloxy group (e.g., a phenoxy group), a carboxy group, an alkoxycarbonyl group, an aryloxycarbonyl group (e.g., a phenoxycarbonyl group), a mercapto group, an alkylthio group, an arylthio group (e.g., a phenylthio group), an amino group with or without substituent (e.g., an amino group, an alkylamino group, a dialkylamino group), an ether bond (—O—), an ester bond (—CO—O—), and a thioether bond (—S—).

In the present invention, a chain compound (e.g., an alkane, an unsaturated aliphatic hydrocarbon) or a chain substituent derived from the chain compound (e.g., an alkyl group, a hydrocarbon group such as an unsaturated aliphatic hydrocarbon group) may be of a straight-chain or branched, unless otherwise stated, and the carbon number thereof may be, for example, 1 to 40, 1 to 32, 1 to 24, 1 to 18, 1 to 12, 1 to 6, or 1 to 2 (two or more in the case of an unsaturated hydrocarbon group). In addition, in the present invention, the number of ring members (the number of atoms constituting the ring) of a cyclic compound (e.g., a cyclic saturated hydrocarbon, a non-aromatic cyclic unsaturated hydrocarbon, an aromatic hydrocarbon, a heteroaromatic compound) or a cyclic group derived from the cyclic compound (e.g., a cyclic saturated hydrocarbon group, a non-aromatic cyclic unsaturated hydrocarbon group, an aryl group, a heteroaryl group) is not particularly limited, and may be, for example, 5 to 32, 5 to 24, 6 to 18, 6 to 12, or 6 to 10. In addition, in the case in which the substituent has an isomer thereof, the isomer may be any isomer unless otherwise stated, and the isomer may be, for example, a 1-naphthyl group or a 2-naphthyl group when merely referred to as a "naphthyl group".

In the present invention, when a compound (e.g., the electron donor-acceptor linked molecule) has an isomer such as a tautomer or a stereoisomer (e.g., a geometric isomer, a conformer, and an optical isomer), any isomer can be used in the present invention, unless otherwise stated. Furthermore, when a compound (e.g., the electron donor-acceptor linked molecule) can form salt, the salt can be used in the present invention, unless otherwise stated. The salt may be an acid addition salt or a base addition salt. Further, the acid forming the acid addition salt may be an inorganic acid or an organic acid, and the base forming the base addition salt may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodine acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxide, alkali metal hydroxide, alkaline earth metal hydroxide, carbonate, and bicarbonate, and specific examples thereof include sodium hydroxide, potassium hydroxide, potassium carbonate, sodium carbonate, sodium hydrogen carbonate, potassium hydrogen carbonate, calcium hydroxide, and calcium carbonate. The organic base also is not particularly limited, and examples thereof include ethanolamine, triethylamine, and tris(hydroxymethyl)aminomethane. The method for producing these salts also is not particularly limited. For example, they can be produced by adding an acid or a base such as described above to the compound as appropriate by a known method.

[2. Halogen Oxide Radical]

Examples of the halogen oxide radical include an oxide radical of a halogen such as $F_2O\cdot$ (oxygen difluoride radical), $F_2O_2\cdot$ (dioxygen difluoride radical), $ClO_2\cdot$ (chlorine dioxide radical), $BrO_2\cdot$ (bromic dioxide radical), and $I_2O_5\cdot$ (iodine oxide (V) radical). Of these, chlorine dioxide radicals are preferred from the viewpoint of cost, ease of handling, reactivity, safety, and the like. The halogen oxide radical may be generated from, for example, a source of the halogen oxide radical (radical generation source) as described below.

[3. Reaction System]

Next, the reaction system is provided. The reaction system is a reaction system containing an aqueous phase (may also be referred to as an "aqueous phase reaction system" hereinafter) as described above. The aqueous phase reaction system may be composed solely of the aqueous phase, or may contain other phases (e.g., a gas phase, an organic phase, and the like). In addition, the aqueous phase may be, for example, a phase in which bubbles are dispersed in water. The bubble is not particularly limited, and may be, for example, a hydrocarbon or a derivative thereof (e.g., a gas such as methane, ethane, or propane) which is the raw material, a source of the halogen oxide radical (e.g., chlorite $HClO_2$ or chlorite ion $ClO_2^-$), the halogen oxide radical (e.g., chlorine dioxide radical $ClO_2\cdot$), another gas (e.g., oxygen gas $O_2$), or two or more of them. The bubbles may be, for example, fine bubbles such as nano-bubbles (bubbles of nanometer size in diameter).

The aqueous phase contains the raw material and the halogen oxide radical. The halogen oxide radical may be generated from the source of the halogen oxide radical, for example, in the halogen oxide radical generation step described below. In this case, for example, the aqueous phase may contain the source of the halogen oxide radical. Further, for example, another aqueous phase containing the source of the halogen oxide radical may be provided.

The source of the halogen oxide radical is, for example, a compound containing oxygen and halogen, and can be halous acid ($HXO_2$) or a salt thereof as a specific example. The salt of the halous acid is not particularly limited, and examples thereof include a metal salt, and examples of the metal salt include alkaline metal salts, alkaline earth metal salts, and rare earth salts. The source of the halogen oxide radical may be, for example, a compound containing oxygen, halogen, and a Group 1 element (e.g., at least one selected from the group consisting of H, Li, Na, K, Rb, and Cs), and can be, for example, the halous acid or an alkaline metal salt thereof. For the halogen oxide radical being the chlorine dioxide radical, the source thereof is not particularly limited and examples thereof include chlorous acid ($HClO_2$) and salts thereof, and specific examples thereof include sodium chlorite ($NaClO_2$), lithium chlorite ($LiClO_2$), potassium chlorite ($KClO_2$), magnesium chlorite ($Mg(ClO_2)_2$), and calcium chlorite ($Ca(ClO_2)_2$). Among them, from the viewpoint of cost, ease of handling, and the like, sodium chlorite ($NaClO_2$) is preferred. Examples of the other sources include bromate such as sodium bromite and iodite such as sodium iodite.

In addition, the aqueous phase may further contain at least one of a Lewis acid and a Brønsted acid, for example. The aqueous phase contains, for example, the source of the halogen oxide radical (e.g., chlorite ion ($ClO_2^-$)) and a Bronsted acid. The aqueous phase is, for example, an aqueous phase in which the source of the halogen oxide radical (e.g., sodium chlorite ($NaClO_2$)) and a Bronsted acid (e.g., hydrochloric acid) are dissolved in water. For example, in a state where the source of the halogen oxide radical and the Bronsted acid are dissolved in the aqueous phase, light irradiation (reaction step) to be described below may be started. Alternatively, in a state where the source of the halogen oxide radical is contained in an aqueous phase, the organic phase and the aqueous phase may be brought into contact with each other, and the halogen oxide radical may be generated by irradiating the aqueous phase with light. Then, by continuing the light irradiation as it is, the reaction step may be performed.

The aqueous phase can be produced by mixing the source of the halogen oxide radical and water, for example. Further, components other than the source of the halogen oxide radical and water may or may not be mixed as appropriate. Examples of such a component include the Lewis acid, the Brønsted acid, and the oxygen ($O_2$).

In the aqueous phase, the concentration of the source of the halogen oxide radical is not particularly limited, and may be, for example, 0.0001 mol/l or more and 1 mol/l or less. The concentration of the source of the halogen oxide radical may be, for example, a concentration converted into a chlorite ion ($ClO_2^-$) concentration in the case of chlorous acid or a salt thereof. The number of moles of the chlorite ion ($ClO_2^-$) may be, for example, $\frac{1}{100000}$ times or more of the number of moles of the raw material (hydrocarbon or derivative thereof) or 1000 times or less.

Only one kind of each of the Lewis acid and Bronsted acid may be used, or a plurality of kinds of the Lewis acid and Bronsted acid may be used in combination. In addition, only one of the Lewis acid and the Brønsted acid may be used or both of them may be used in combination, or one substance may serve as both of the Lewis acid and the Brønsted acid. Note that, in the present invention, the "Lewis acid" refers to, for example, a substance which serves as a Lewis acid for the source of the halogen oxide radical.

The concentration of at least one of the Lewis acid and the Bronsted acid in the aqueous phase is not particularly limited, and can be set as appropriate according to, for example, the type of the raw material (substrate) and the target product (oxidation reaction product), and may be, for example, 0.0001 mol/l or more and 1 mol/l or less.

The Lewis acid may be, for example, an organic substance or an inorganic substance. Examples of the organic substance include ammonium ions and organic acids (e.g., carboxylic acid). The inorganic substance may contain one or both of metal ions and non-metal ions. The metal ion may include one or both of a typical metal ion and a transition metal ion.

The inorganic substance is, for example, at least one selected from the group consisting of alkaline earth metal ions (e.g., $Ca^{2+}$), rare earth ions, $Mg^{2+}$, $Sc^{3+}$, $Li^+$, $Fe^{2+}$, $Fe^{3+}$, $Al^{3+}$, silicate ions, and borate ions. Examples of the alkaline earth metal ion include calcium, strontium, barium, and radium ions. Specific examples of alkaline earth metal ion include $Ca^{2+}$, $Sr^{2+}$, $Ba^{2+}$, and $Ra^{2+}$. Further, the "rare earth" is a generic term for a total of 17 elements including the two elements of scandium $_{21}Sc$, yttrium $_{39}Y$, and 15 elements (lanthanoid) from lanthanum $_{57}La$ to rutetium $_{71}Lu$. Examples of the rare earth ion include trivalent cations corresponding to the 17 elements. Examples of the counter ion of the Lewis acid include trifluoromethanesulfonate ion (also referred to as $CF_3SO_3^-$ or $OTf^-$), trifluoroacetate ion ($CF_3COO^-$), acetate ion, fluoride ion, chloride ion, bromide ion, iodide ion, sulfate ion, hydrogen sulfate ion, sulfite ion, nitrate ion, nitrite ion, phosphate ion, and phosphite ion. For example, the Lewis acid may be scandium triflate (Sc $(OTf)_3$) or the like.

Further, the Lewis acid (including counter ion) may be at least one selected from the group consisting of $AlCl_3$, $AlMeCl_2$, $AlMe_2Cl$, $BF_3$, $BPh_3$, $BMe_3$, $TiCl_4$, $SiF_4$, and $SiCl_4$, for example. It is to be noted that the "Ph" denotes a phenyl group and the "Me" denotes a methyl group.

The Lewis acidity of the Lewis acid is, for example, 0.4 eV or more, but is not limited thereto. The upper limit of the Lewis acidity is not particularly limited, and is, for example, 20 eV or less. Note that the Lewis acidity can be measured by the method described in Ohkubo, K.; Fukuzumi, S. Chem. Eur. J., 2000, 6, 4532, J. Am. Chem. Soc. 2002, 124, 10270-10271, or J. Org. Chem. 2003, 68, 4720-4726, for example. Specifically, the Lewis acidity can be measured by the following method.

(Measurement Method of Lewis Acidity)

As to acetonitrile (MeCN) containing cobalt tetraphenylporphyrin, saturated $O_2$, and an object whose Lewis acidity is to be measured (e.g., cations such as metals and represented by $M^{n+}$ in the chemical reaction formula (1a) below) in the chemical reaction formula (1a) below, the change in the ultraviolet-visible absorption spectrum at room temperature is measured. On the basis of the obtained reaction rate constant ($k_{cat}$), the $\Delta E$ value (eV), which is an indicator of the Lewis acidity, can be calculated. The higher the $k_{cat}$, the stronger the Lewis acidity. Furthermore, the Lewis acidity of an organic compound can be estimated from the energy level of the lowest unoccupied molecular orbital (LUMO) calculated by the quantum chemical calculation. The higher the value at the positive side, the stronger the Lewis acidity.

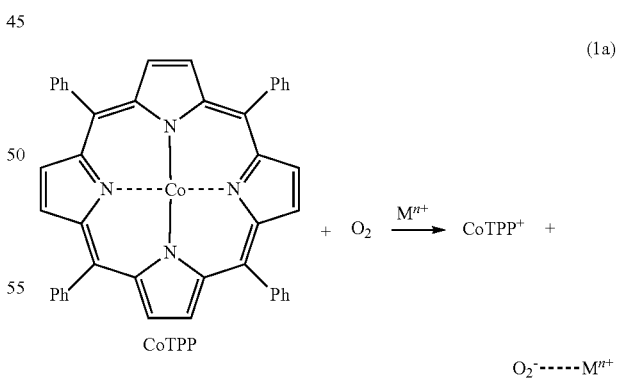

(1a)

The Bronsted acid is not particularly limited and examples thereof include inorganic acids and organic acids, and specific examples thereof include trifluoromethanesulfonic acid, trifluoroacetic acid, acetic acid, hydrofluoric acid, hydrogen chloride, hydrobromic acid, hydroiodic acid, sulfuric acid, sulfurous acid, nitric acid, nitrous acid, phosphoric acid, and phosphorous acid. The Bronsted acid has an acid dissociation constant $pK_a$ of, for example, 10 or less. The lower limit of the $pK_a$ is not particularly limited, and is, for example, −10 or more.

As for the oxygen ($O_2$), for example, oxygen may be dissolved by blowing air or oxygen gas into at least one of the water and the organic phase before or after adding the source of the halogen oxide radical, the Lewis acid, the Brønsted acid, the reaction substrate (raw material), and the like. At this time, for example, the water may be saturated with oxygen ($O_2$). By allowing at least one of the aqueous phase and the organic phase to contain the oxygen ($O_2$), for example, the oxidation reaction of a hydrocarbon or a derivative thereof, which is the raw material (substrate), can further be promoted.

In the present invention, as described above, the Lewis acid, the Bronsted acid, the radical generation source, or the like may or may not be dissolved in the water in the aqueous phase. For example, the production method of the present invention may be performed in a state where the Lewis acid, the Bronsted acid, the radical generation source, or the like is dispersed or precipitated in the water.

[4. Halogen Oxide Radical Generation Step]

Next, in the production method of the present invention, as described above, a halogen oxide radical generation step of generating the halogen oxide radical may be performed.

The halogen oxide radical generation step is not particularly limited. The halogen oxide radical generation step is described below mainly with reference to a case in which the halogen oxide radical is a chlorine dioxide radical by way of example. The halogen oxide radical generation step, however, is not limited thereto.

The halogen oxide radical generation step may be performed, for example, by dissolving the chlorine dioxide radical generation source (e.g., chlorite or a salt thereof) in water and allowing the resultant to stand still, thereby naturally generating chlorine dioxide radical from chlorite ion. At this time, for example, the presence of at least one of the Lewis acid and the Brønsted acid in the water further promotes the generation of chlorine dioxide radical. Further, for example, as described above, the chlorine dioxide radical may be generated by irradiating the aqueous phase with light. However, as described above, the chlorine dioxide radicals can be generated by simply allowing the aqueous phase to stand still without performing light irradiation.

The mechanism by which the chlorine dioxide radical is generated from the chlorite ion in water is presumed, for example, as in the Scheme 1 below. The Scheme 1 below, however, is an example of a presumed mechanism and does not limit the present invention in any way. The first (uppermost) reaction formula in the Scheme 1 below shows a disproportionation reaction of chlorite ion ($ClO_2^-$), and it is considered that the presence of at least one of a Lewis acid and a Brønsted acid in water facilitates the movement of the equilibrium to the right. The second (middle) reaction formula in the Scheme 1 below shows a dimerization reaction, and hypochlorite ion ($ClO^-$) generated in the first reaction formula reacts with chlorite ion to generate dichlorine dioxide ($Cl_2O_2$). It is considered that the greater the protons $H^+$ in water, i.e., the more acidic, the easier the process is to proceed. The third (lowermost) reaction formula in the Scheme 1 below shows radical generation. In this reaction, the dichlorine dioxide generated in the second reaction formula reacts with a chlorite ion to produce a chlorine dioxide radical.

Scheme 1

Disproportionation reaction

Dimerization reaction

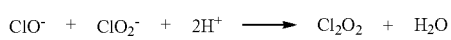

Radical generation

In the next step (reaction step), when the aqueous phase reaction system is used, for example, the chlorine dioxide radical may be generated in the aqueous phase reaction system, and then the aqueous phase reaction system may be subjected to the reaction step as it is.

[4. Reaction Step]

Subsequently, the reaction step is performed. The reaction system used in the reaction step is an aqueous phase reaction system, as described above. The reaction step is described below mainly with reference to a case in which the halogen oxide radical is a chlorine dioxide radical by way of example. The reaction step can be performed in the same manner, for example, when the halogen oxide radical is other than chlorine dioxide radical.

First, prior to performing the reaction step, the raw material and the halogen oxide radical (e.g., chlorine dioxide radical) are caused to be contained in the aqueous phase. The raw material and the halogen oxide radical may be dissolved in the aqueous phase, for example, or may be dispersed, suspended, or the like in the aqueous phase.

Next, in the reaction step, for example, as described above, the aqueous phase is irradiated with light. The case in which chlorine dioxide radical ($ClO_2\cdot$) in the aqueous phase is irradiated with light is predicted to be as shown in FIG. 1, for example. FIG. 1 shows the result of the density functional calculation by UCAM-B3LYP/6-311+G(d, p) def2TZV. The left side of FIG. 1 shows the state of chlorine dioxide radical ($ClO_2\cdot$) molecule before light irradiation, and the right side of FIG. 1 shows the state of chlorine dioxide radical ($ClO_2\cdot$) molecule after light irradiation. As shown in FIG. 1, before light irradiation, two oxygen atoms O are each bound to chlorine atom Cl, and the bond length of Cl—O is 1.502 Å (0.1502 nm). On the other hand, after light irradiation, only one oxygen atom O is bound to the chlorine atom Cl, the bond length of Cl—O is 2.516 Å (0.2516 nm), and the other oxygen atom is bound to the one oxygen atom. Thus, it is considered that Cl—O bond is cleaved and chlorine radical (Cl·) and oxygen molecule ($O_2$) are generated. FIG. 1, however, is merely an example of the prediction of the calculation result and does not limit the present invention in any way.

It is considered that the reaction occurring in the reaction step is, for example, as follows. First, chlorite ions ($ClO_2^-$) in the aqueous layer (aqueous phase) react with acid to generate chlorine dioxide radicals ($ClO_2\cdot$). Next, the aqueous phase containing the chlorine dioxide radicals (ClO$_2$·) is irradiated with light to give light energy hv (h is a Planck constant and v is a frequency of light), whereby the chlorine dioxide radicals (ClO$_2$·) in the aqueous phase are decomposed to generate chlorine radicals (Cl·) and an oxygen molecule (O$_2$). Thus, the raw material (substrate) is oxidized to produce an oxidation reaction product (e.g., alcohol). For example, when the oxidation reaction product is water-soluble (e.g., water-soluble alcohol), it is dissolved in the aqueous phase. This description, however, is merely an example, and does not limit the present invention in any way. For example, the oxidation reaction product is not limited to a water-soluble alcohol, and may be any oxidation reaction product. For example, the oxidation reaction product may be non-water soluble.

In the reaction step, the wavelength of the irradiation light is not particularly limited, and may be, for example, 200 nm or more and 800 nm or less. The light irradiation time is not particularly limited, and may be, for example, 1 min or more and 1000 h or less. The reaction temperature is not particularly limited, and may be, for example, 0° C. or more and 100° C. or less. The atmospheric pressure at the time of reaction is not particularly limited, and may be, for example, 0.1 MPa or more and 100 MPa or less. According to the present invention, for example, as described in the Examples to be described below, the reaction step or all the steps including the reaction step can be performed at ordinary temperature (room temperature) and a normal pressure (atmospheric pressure) without heating, pressurizing, depressurizing, or the like at all. It is to be noted that the "room temperature" is not particularly limited, and is, for example, 5 to 35° C. Furthermore, according to the present invention, for example, as described in the Examples to be described below, the reaction step or all the steps including the reaction step can be performed in a normal-atmosphere environment without performing inert gas substitution or the like.

In the light irradiation, the light source is not particularly limited. For example, excitation can be performed easily by using visible light contained in natural light such as sunlight, for example. Further, for example, a light source such as a xenon lamp, a halogen lamp, a fluorescent lamp, or a mercury lamp may or may not be used as appropriate instead of or in addition to the natural light. Further, a filter for cutting wavelengths other than the necessary wavelengths may or may not be used as appropriate.

The mechanism by which ethanol is generated by an oxidation reaction of ethane is presumed, for example, as in the Scheme 2 below. The Scheme 2 below, however, is merely an example of a presumed mechanism and does not limit the present invention in any way. Specifically, as shown in FIG. 1, chlorine dioxide radicals are decomposed by light irradiation to generate chlorine radicals (Cl·) and an oxygen molecule (O$_2$). The chlorine radicals act as a hydrogen-withdrawing agent against ethane to generate ethyl radicals (CH$_3$CH$_2$·). Then, the oxygen molecule oxidizes the ethyl radical as shown in the Scheme 2, thereby generating ethanol.

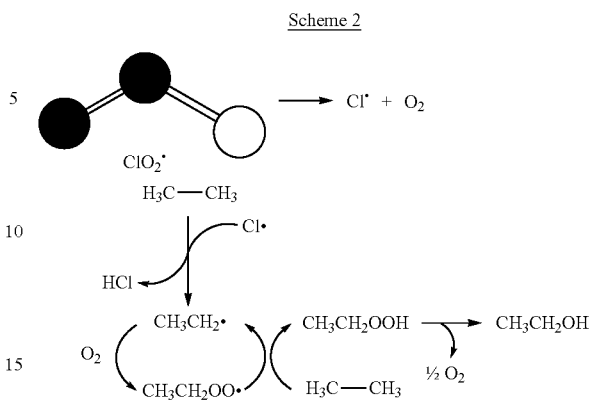

Scheme 2

The reaction formula of the case where methanol and formic acid are generated by an oxidation reaction of methane using sodium chlorite is, for example, as the following Scheme 3. It is to be noted, however, that the Scheme 3 is merely an example and the oxidation reaction of methane using the present invention is not limited thereto.

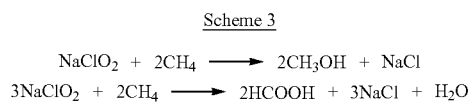

The mechanism by which methanol is generated by an oxidation reaction of methane is presumed, for example, as in the Scheme 4 below. The Scheme 4 below, however, is merely an example of a presumed mechanism and does not limit the present invention in any way. Specifically, in the same manner as in the case in which ethanol is generated from ethane, first, chlorine dioxide radicals are decomposed by light irradiation to generate chlorine radicals (Cl·) and an oxygen molecule (O$_2$). The chlorine radicals act as a hydrogen-withdrawing agent against methane to generate methyl radicals (CH$_3$·). Then, the oxygen molecule oxidizes the methyl radical as shown in the Scheme 4, thereby generating methanol.

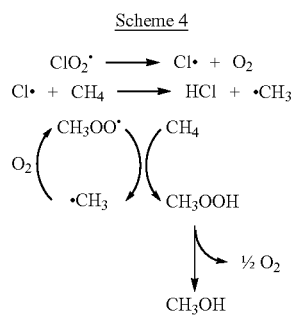

As an oxidation reaction of methane, for example, a reaction shown in Scheme 5 below is also conceivable. This, however, is also merely an example, and does not limit the present invention in any way.

Scheme 5

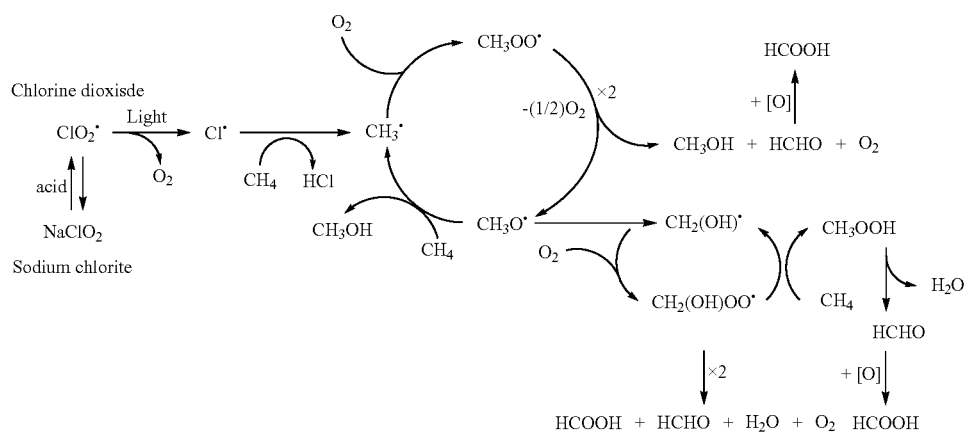

In addition, in the present invention, the raw material (substrate) is not limited only to ethane or methane, and may be a freely selected hydrocarbon or a derivative thereof as described above. Examples of the hydrocarbon or the derivative thereof, which is a raw material (substrate), are as described above, for example.

In the present invention, for example, as in the Scheme A below, the raw material may be represented by the following chemical formula (A1), and the oxidation reaction product thereof may be at least one of an alcohol represented by the following chemical formula (A2) and a carboxylic acid represented by the following chemical formula (A3). In the Scheme A, Rs are each a freely selected atom or atomic group, and may be, for example, a hydrogen atom, a hydrocarbon group, or a derivative thereof. The hydrocarbon group can be any group. For example, the hydrocarbon group may be a straight-chain or branched and saturated or unsaturated, and may or may not have a ring structure, and the ring structure may be an aromatic ring or a non-aromatic ring. Also, for example, in the Scheme A below, the oxidation reaction product may contain aldehyde in addition to or instead of at least one of alcohol and carboxylic acid.

Scheme A

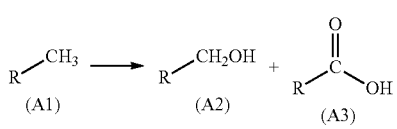

In the Scheme A, when the raw material (substrate) (A1) is methane, for example, as in the Scheme A1 below, the oxidation reaction product may contain at least one of methanol and formic acid. In addition, when the raw material (substrate) (A1) is ethane, for example, as in the Scheme A2 below, the oxidation reaction product may contain at least one of ethanol and acetic acid. The Schemes A1 and A2, however, are merely examples, and the oxidation reaction of methane or ethane is not limited thereto in the production method of the present invention.

Scheme A1

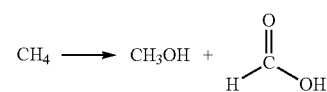

Scheme A2

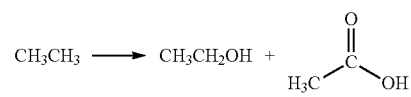

Further, for example, as in the Scheme B below, the raw material may be represented by the following chemical formula (B1), and the oxidation reaction product thereof may be at least one of an alcohol represented by the following chemical formula (B2) and a carbonyl compound represented by the following chemical formula (B3) (e.g., a ketone). In the Scheme B, Rs are each a freely selected atom or atomic group, and may be, for example, a hydrocarbon group or a derivative thereof. The hydrocarbon group can be any group. For example, the hydrocarbon group may be a straight-chain or branched and saturated or unsaturated, and may or may not have a ring structure, and the ring structure may be an aromatic ring or a non-aromatic ring. Rs may be identical to or different from each other. Further, for example, in each of the following chemical formulae (B1), (B2) and (B3), two Rs may together form a ring structure together with a carbon atom to which they are bound.

Scheme B

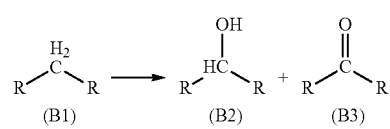

In the Scheme B, when the raw material (substrate) (B1) is cyclohexane, for example, as in the Scheme B1 below, the oxidation reaction product may contain at least one of cyclohexanol and cyclohexanone. The Scheme B1, however, is merely an example and the oxidation reaction of cyclohexane is not limited thereto in the production method of the present invention.

Scheme B1

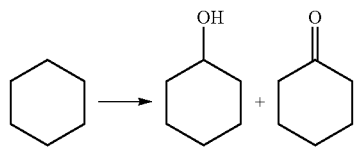

In the present invention, for example, as in the Scheme C below, the raw material is an aromatic compound represented by the following chemical formula (C1), and the oxidation reaction product thereof may be at least one of a phenol represented by the following chemical formula (C2) and a quinone represented by the following chemical formula (C3). In the Scheme C, Rs are each a freely selected atom or atomic group, and may be, for example, a hydrogen atom, a hydrocarbon group, or a derivative thereof. The hydrocarbon group can be any group. For example, the hydrocarbon group may be a straight-chain or branched and saturated or unsaturated, and may or may not have a ring structure, and the ring structure may be an aromatic ring or a non-aromatic ring. Rs may be identical to or different from each other. Further, for example, in each of the following chemical formulae (C1), (C2) and (C3), two or more Rs may together form a ring structure together with a benzene ring to which they are bound. The Scheme C, however, is merely an example, and does not limit the present invention. In other words, as described above, in the production method of the present invention, an aromatic compound, which is a raw material (substrate), is not limited to the following chemical formula (C1), and the oxidation reaction product of the aromatic compound is not limited to the following formulae (C2) and (C3).

Scheme C

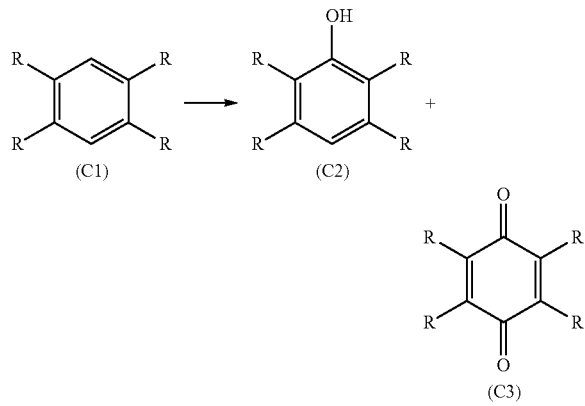

In the Scheme C, when the raw material (substrate) (C1) is benzene, for example, as in the Scheme C1 below, the oxidation reaction product may contain at least one of hydroxybenzene and p-benzoquinone. The Scheme C1, however, is merely an example, and the oxidation reaction of benzene is not limited thereto in the production method of the present invention.

Scheme C1

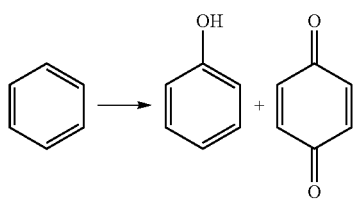

In the case where the raw material (substrate) is an aromatic compound, it is preferable that an electron donor group is bound to an aromatic ring of the raw material aromatic compound, because this allows an oxidation reaction (including an oxidative substitution reaction) of the raw material aromatic compound to proceed more easily. The number of the electron donor groups may be one or more, and the electron donor group with a strong electron donating property is preferable. More specifically, it is more preferable that at least one substituent selected from the group consisting of $-OR^{100}$, $-NR^{200}_2$, and $Ar^{100}$ is covalently bound to the aromatic ring. $R^{100}$ may be a hydride atom or a freely selected substituent. If there are a plurality of $R^{100}$, $R^{100}$ may be identical to or different from each other. $R^{200}$ is a hydrogen atom or a freely selected substituent, and $R^{200}$ may be identical to or different from each other. $Ar^{100}$ is an aryl group. When there are a plurality of $Ar^{100}$, $Ar^{100}$ may be identical to or different from each other.

$Ar^{100}$ may be a group derived from a freely selected aromatic ring such as a benzene ring, a naphthalene ring, an anthracene ring, a phenanthrene ring, a pyridine ring, a thiophene ring, a pyrene ring, or the like. The aromatic ring may further have one or more substituents on the ring, and the substituents may be identical to or different from each other when there are a plurality of substituents. $Ar^{100}$ may be a phenyl group, for example.

$R^{100}$ preferably is at least one selected from the group consisting of a hydrogen atom, an alkyl group, an aryl group, and an acyl group. The alkyl group preferably is a straight-chain or branched alkyl group having 1 to 6 carbon atoms, and a methyl group is particularly preferred. The acyl group preferably is a straight-chain or branched acyl group having 1 to 6 carbon atoms. The aryl group is the same as $Ar^{100}$, for example, and is a phenyl group, for example.

$R^{200}$ preferably is at least one selected from the group consisting of a hydrogen atom, an alkyl group, an aryl group, and an acyl group. The alkyl group preferably is a straight-chain or branched alkyl group having 1 to 6 carbon atoms, and a methyl group is particularly preferred. The acyl group preferably is a straight-chain or branched acyl group having 1 to 6 carbon atoms. The aryl group is the same as $Ar^{100}$, for example, and is a phenyl group, for example. As the $-NR^{200}_2$, an amino group substituted with an electron donating substituent such as a dimethylamino group, a diphenylamino group, or the like is particularly preferable because of its high electron donating property.

In addition, in the aromatic compound that is a raw material (substrate), for example, a substituent such as an alkyl group is covalently bound to an aromatic ring, and the substituent may be oxidized by the reaction step. For example, the oxidizing agent may contain an oxygen atom, the aromatic compound may contain a methylene group ($-CH_2-$) covalently bound to an aromatic ring, and the methylene group ($-CH_2-$) may be oxidized to convert into a carbonyl group ($-CO-$) in the reaction step. In this case, an atom or an atomic group that is bound to the methylene group and the carbonyl group is not particularly limited, and examples thereof include a hydrogen atom, an alkyl group, and an aryl group. The alkyl group preferably is a straight-chain or branched alkyl group having 1 to 6 carbon atoms. The alkyl group and the aryl group may be further substituted with one or more substituents, and the substituents may be identical to or different from each other when there are a plurality of substituents. For example, the methylene group becomes a methyl group (—CH$_3$) when hydrogen is bound thereto, and it becomes a formyl group (—CHO) after oxidation. The methylene group becomes an ethyl group (—CH$_2$CH$_3$) when a methyl group is bound thereto, and it becomes an acetyl group (—COCH$_3$) after oxidation. The methylene group becomes a benzyl group (—CH$_2$Ph) when a phenyl group is bound thereto, and it becomes a benzoyl group (—COPh) after oxidation. Further, for example, the substituent (before being oxidized) covalently bound to an aromatic ring may be a formyl group (—CHO) and it may become a carboxy group (—COOH) after oxidation.

Further, for example, the raw material (substrate) may be an olefin, and the olefin may be, for example, an aromatic olefin or an aliphatic olefin. The olefin may be, for example, an olefin represented by the chemical formula (D1) in the Scheme D below. Further, the oxidation reaction product of the olefin is not particularly limited, and may contain at least one of epoxide and diol, for example, as in the Scheme D below. In the following chemical formulae (D1), (D2) and (D3), Rs are each a hydrogen atom or a freely selected substituent, and Rs may be identical to or different from each other. The freely selected substituent is, for example, an alkyl group, an unsaturated aliphatic hydrocarbon group, an aryl group, a heteroaryl group, a halogen, a hydroxy group (—OH), a mercapto group (—SH), or an alkylthio group (—SR, R is an alkyl group), and may be substituted or unsubstituted with a further substituent. The alkyl group preferably is a straight-chain or branched alkyl group having 1 to 6 carbon atoms. Further, the olefin which is a substance to be oxidized may be an olefin containing only one olefin bond (carbon-carbon double bond), or may be an olefin containing a plurality of (two or more) olefin bonds.

Scheme D

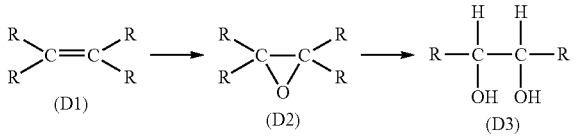

(D1)     (D2)     (D3)

The olefin may be, for example, an aromatic olefin. In other words, for example, in the chemical formula (D1), at least one of Rs may be an aromatic ring (an aryl group or a heteroaryl group). In the present invention, the aromatic olefin is not particularly limited. It is preferable that an electron donor group is bound to an aromatic ring of the aromatic olefin, for example, because this allows an oxidation reaction (including an oxidative substitution reaction) of the aromatic olefin to proceed more easily. The number of the electron donor groups may be one or more, and the electron donor group with a strong electron donating property is preferable. More specifically, it is more preferable that at least one substituent selected from the group consisting of —OR$^{100}$, —NR$^{200}$$_2$, and Ar$^{100}$ is covalently bound to the aromatic ring.

In the method for producing an oxidation reaction product of the present invention, the olefin may be at least one selected from the group consisting of ethylene, propylene, styrene, and butadiene. Further, the oxidation reaction product may be, for example, at least one of epoxide and diol as described above. The examples thereof are shown in the following Schemes D1 to D3. The Schemes D1 to D3, however, are merely examples, and the oxidation reactions of ethylene, propylene, and styrene are not limited thereto in the present invention.

Scheme D1

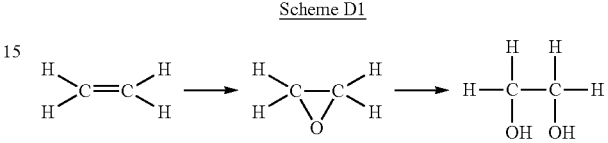

Scheme D2

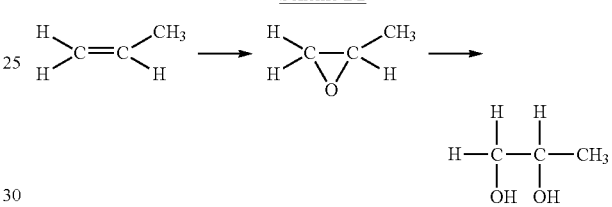

Scheme D3

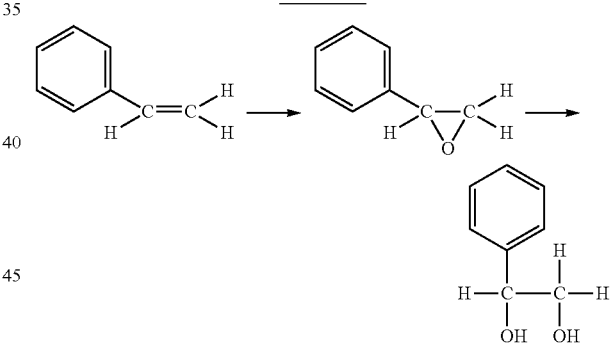

In the production method of the present invention, the ratio between the obtained oxidation reaction products (e.g., the ratio between alcohol and carboxylic acid, the ratio between phenol and quinone) can be adjusted by appropriately setting the reaction conditions.

Furthermore, in the production method of the present invention, the oxidation reaction product of the raw material (substrate) is not limited to the alcohol, carboxylic acid, aldehyde, ketone, phenol, quinone, or the like. In addition to or instead of them, for example, a chlorinated product or the like of the raw material (substrate) may be contained. For example, when the chlorine atom radical Cl· in the gas phase reaction of hydrocarbon is bimolecularly involved (e.g., gas phase reaction using chlorine gas Cl$_2$), even in the presence of oxygen molecule O$_2$, chlorination is presumed to occur preferentially. In the production method of the present invention, although chlorine atom radical Cl· and oxygen molecule O$_2$ are generated by decomposition of chlorine dioxide radical, since the reaction is performed in a liquid phase, chlorination of the substrate is suppressed, and the alcohol, carboxylic acid, aldehyde, ketone, phenol, quinone, and the like are presumed to be preferentially generated. These presumptions are merely examples, and do not limit the present invention in any way. Furthermore, according to the present invention in which the reaction is performed in a biphasic system containing an aqueous phase and an organic phase, even the oxidation reaction of hydrocarbon gas (e.g., methane, ethane), which has been difficult to be performed in a liquid phase, can be performed efficiently in a liquid phase. Thus, an oxidation reaction product (e.g., methanol, formic acid, ethanol, acetic acid) of the hydrocarbon gas of great use for industrial application can be produced efficiently from the hydrocarbon gas.

Furthermore, after the reaction step, the step of recovering the oxidation reaction product is performed as necessary. The recovery step is not particularly limited, and for example, a method similar to that of a common organic synthesis reaction may be used. Specifically, for example, a method such as extraction with an organic solvent, distillation, fractionation, or filtration may be used as appropriate to recover the oxidation reaction product from the reaction system. Furthermore, the recovered oxidation reaction product is isolated and purified as necessary. The method of isolating and purifying the recovered oxidation reaction product is not particularly limited, and can be performed as appropriate by distillation, filtration, or the like according to a common organic synthesis reaction.

According to the present invention, for example, by a very simple method of simply irradiating a chlorine dioxide radical aqueous solution with light, chlorine atom radical Cl· and oxygen molecule $O_2$ can be generated, thereby performing the oxidation reaction. Furthermore, by such a simple method, for example, a hydrocarbon or a derivative thereof can be converted into an oxidation reaction product efficiently even under very mild conditions such as ordinary temperature and normal pressure.

Furthermore, according to the present invention, the oxidation reaction product of the raw material (a hydrocarbon or a derivative thereof) can be obtained without using toxic heavy metal catalysts and the like. This allows the oxidation reaction product to be obtained efficiently by a method with very small burden to the environment in addition to the fact that the reaction can be performed under very mild conditions such as ordinary temperature and normal pressure as described above.

The production method of the present invention can be performed at low cost in a simple manner, for example. Specifically, for example, it is also possible to perform the reaction at room temperature and atmospheric pressure without requiring high temperature, high pressure, and the like. Therefore, for example, a reaction can be performed without requiring a special reaction vessel, a facility, or the like, and scale-up of the reaction volume is also easy. Further, for example, it is also possible to produce a halogen oxide radical using sodium chlorite or the like, which is excellent in safety and inexpensive, and to perform the reaction. According to the production method of the present invention, for example, methanol, formic acid, and the like widely used in the market can be produced at low cost and safely, so that the industrial utility value of the present invention is huge. The field of use of the present invention is not particularly limited, and the present invention is widely available, for example, in the same fields as the general fields of use of the oxidation reaction product of the aforementioned raw material. The production method of the present invention is available, for example, for fuel synthesis, synthesis of chemical raw materials, and the like.

EXAMPLES

Examples of the present invention will be described below in more detail. The present invention, however, is by no means limited thereby.

Example 1

Heavy water ($D_2O$) was placed in a 5 ml-volume glass vessel. In this $D_2O$, 1 mM (mM denotes mmol/l; the same applies hereinafter) of methane ($CH_4$), 1 mM of sodium chlorite ($NaClO_2$), and 1 mM of oxygen gas ($O_2$) were dissolved to prepare an aqueous solution (aqueous phase reaction system). The aqueous solution was irradiated with light using a 500 W Xe lamp for 2 hours at room temperature (about 25° C.) and at atmospheric pressure. In this way, the chlorine dioxide radical generation (halogen oxide radical generation step) from the sodium chlorite and the reaction of the methane and the chlorine dioxide radical (reaction step) were simultaneously performed. The reaction was tracked by $^1H$ NMR. After 2 hours of light irradiation, $^1H$ NMR confirmed the generation of methanol and formic acid, which are the oxidation reaction products of raw material (methane). The yield of the oxidation reaction product based on the raw material (methane) was calculated from the peak intensity of $^1H$ NMR, and it was found that methanol was 5% and formic acid was 25%.

Further, for comparison, when the experiment was performed for 2 hours in the same manner as in Example 1 except that light irradiation was not performed, no reaction (yield of oxidation reaction product was 0%) occurred. Further, when light irradiation was performed for 2 hours under the same conditions as in Example 1 except that sodium chlorite ($NaClO_2$) was not used, no reaction occurred.

Example 2

Oxidization reaction of ethane was performed in an aqueous phase in the same manner as in Example 1 except that 1 mM of ethane ($C_2H_6$) was used instead of 1 mM of methane ($CH_4$). After 2 hours of light irradiation, $^1H$ NMR confirmed the generation of ethanol and acetic acid, which are the oxidation reaction products of raw material (ethane). The yield of the oxidation reaction product based on the raw material (ethane) was calculated from the peak intensity of $^1H$ NMR, and it was found that ethanol was 8% and acetic acid was 32%.

Further, for comparison, when the experiment was performed for 2 hours in the same manner as in Example 2 except that light irradiation was not performed, no reaction (yield of oxidation reaction product was 0%) occurred. Further, when light irradiation was performed for 2 hours under the same conditions as in Example 2 except that sodium chlorite ($NaClO_2$) was not used, no reaction occurred.

Example 3

Oxidization reaction of propane was performed in an aqueous phase in the same manner as in Example 1, except that 1 mM of propane ($C_3H_8$) was used instead of 1 mM of methane ($CH_4$). After 2 hours of light irradiation, $^1H$ NMR confirmed the generation of 2-propanol (isopropyl alcohol), propionate, and acetone, which are the oxidation reaction products of raw material (propane). The yield of the oxidation reaction product based on the raw material (propane) was calculated from the peak intensity of $^1$H NMR, and it was found that 2-propanol was 1%, propionic acid was 18%, and acetone was 45%.

Further, for comparison, when the experiment was performed for 2 hours in the same manner as in Example 3 except that light irradiation was not performed, no reaction (yield of oxidation reaction product was 0%) occurred. Further, when light irradiation was performed for 2 hours under the same conditions as in Example 3 except that sodium chlorite ($NaClO_2$) was not used, no reaction occurred.

As shown in Examples 1 to 3, it was possible to efficiently produce an oxidation reaction product such as an alcohol, a carboxylic acid, a ketone, or the like from a hydrocarbon simply by light irradiation in a normal-atmosphere environment at ordinary temperature and a normal pressure. It is to be noted that, while a xenon lamp was used as a light source in the Examples, use of sunlight, LED, or the like as a light source achieves further energy saving and cost reduction.

Further, as shown in Examples 1 to 3, according to the present invention, it is possible to efficiently obtain an oxidation reaction product having extremely high industrial utility value using a hydrocarbon as a raw material (substrate). For example, all of the methanol and formic acid obtained in Example 1 and the ethanol and acetic acid obtained in Example 2 are of great utility for various applications such as fuels, solvents, and raw materials of chemical products. In other words, the Examples demonstrated that the present invention has a huge value from the viewpoint of industrial application.

INDUSTRIAL APPLICABILITY

As described above, according to the production method of the present invention, an oxidation reaction product of a hydrocarbon or a derivative thereof can be produced in an aqueous phase using a hydrocarbon or a derivative thereof as a raw material. According to the present invention, for example, by a very simple method of simply performing light irradiation, a hydrocarbon or a derivative thereof can be converted into an oxidation reaction product efficiently even under very mild conditions such as ordinary temperature and normal pressure. Furthermore, according to the present invention, using a hydrocarbon or a derivative thereof as a raw material, oxidation reaction products of great use for industrial application, such as alcohol, carboxylic acid, ketone, phenol, and quinone can be produced efficiently. Since such oxidation reaction products conventionally could not be obtained efficiently using a hydrocarbon as a raw material, it was very difficult to make effective use of hydrocarbon such as natural gas as a raw material. In contrast, the present invention can make effective use of hydrocarbon such as natural gas as a raw material. According to the present invention, a compound which conventionally had to be synthesized using petroleum as a raw material can be synthesized efficiently using natural gas as a raw material by a very simple method. Thus, the present invention can make a significant contribution to energy issues and the like. Furthermore, according to the first aspect, oxidation reaction products of the raw material (the hydrocarbon or a derivative thereof) can be obtained without using toxic heavy metal catalysts and the like. Furthermore, according to the present invention, the oxidation reaction product of the raw material (a hydrocarbon or a derivative thereof) can be obtained without using toxic heavy metal catalysts and the like. This allows the oxidation reaction product to be obtained efficiently by a method with very small burden to the environment in addition to the fact that the reaction can be performed under very mild conditions such as ordinary temperature and normal pressure as described above. Accordingly, the industrial value of the present invention is enormous.

This application claims priority from Japanese Patent Application No. 2018-117453 filed on Jun. 20, 2018. The entire subject matter of the Japanese Patent Applications is incorporated herein by reference.

The invention claimed is:

1. A method for producing an oxidation reaction product comprising a step of:
   irradiating a reaction system with light to cause a reaction of a raw material and a halogen oxide radical, wherein the raw material is a hydrocarbon or a derivative thereof,
   the reaction system is a reaction system comprising an aqueous phase and being free from an organic phase,
   the aqueous phase comprises the raw material and the halogen oxide radical, and
   in the reaction, the raw material is oxidized by the light irradiation to produce an oxidation reaction product of the raw material.

2. The method according to claim 1, wherein in the reaction, at least the aqueous phase is irradiated with light.

3. The method according to claim 1, wherein the halogen oxide radical is a chlorine dioxide radical.

4. The method according to claim 1, further comprising a step of:
   generating the halogen oxide radical.

5. The method according to claim 4, wherein a reaction system of the halogen oxide radical generation step comprises an aqueous phase, and
   in the halogen oxide radical generation step, the aqueous phase comprises a source of the halogen oxide radical and the halogen oxide radical is generated from the source of the halogen oxide radical.

6. The method according to claim 4, wherein in the halogen oxide radical generation step, at least one of a Lewis acid or a Brønsted acid is caused to act on the source of the halogen oxide radical to generate the halogen oxide radical.

7. The method according to claim 4, wherein the halogen oxide radical is a chlorine dioxide radical, and in the halogen oxide radical generation step, the source of the chlorine dioxide radical is chlorite ion ($ClO_2^-$).

8. The method according to claim 1, wherein the reaction is performed in a state where oxygen ($O_2$) is present in the reaction system.

9. The method according to claim 1, wherein the method is performed in an atmosphere having a temperature of 0 to 40° C. and a pressure of 0.1 to 1.0 MPa.

10. The method according to claim 1, wherein the raw material is at least one selected from the group consisting of methane, ethane, and propane.

11. The method according to claim 1, wherein the oxidation reaction product of the raw material is at least one selected from the group consisting of alcohols, carboxylic acids, aldehydes, ketones, percarboxylic acids, and hydroperoxides.

\* \* \* \* \*